US012357197B2

(12) United States Patent
Comtois et al.

(10) Patent No.: US 12,357,197 B2
(45) Date of Patent: Jul. 15, 2025

(54) PATIENT MONITORING SYSTEM FOR DETERMINING MOVEMENT ACTIVITY

(71) Applicant: Avent, Inc., Alpharetta, GA (US)

(72) Inventors: Marc Comtois, Irvine, CA (US); Arne Jorgen Madsen, Newport Beach, CA (US); Steve S. Khalaj, Laguna Hills, CA (US); Joost L. Mulders, Costa Mesa, CA (US); Bridget F. Kuske, Newport Beach, CA (US)

(73) Assignee: Avent, Inc., Alpharetta, GA (US)

( * ) Notice: Subject to any disclaimer, the term of this patent is extended or adjusted under 35 U.S.C. 154(b) by 375 days.

(21) Appl. No.: 17/268,496

(22) PCT Filed: Aug. 21, 2019

(86) PCT No.: PCT/US2019/047406
§ 371 (c)(1),
(2) Date: Feb. 15, 2021

(87) PCT Pub. No.: WO2020/046660
PCT Pub. Date: Mar. 5, 2020

(65) Prior Publication Data
US 2021/0236025 A1    Aug. 5, 2021

Related U.S. Application Data

(60) Provisional application No. 62/724,364, filed on Aug. 29, 2018.

(51) Int. Cl.
*A61B 5/11* (2006.01)
*A61B 5/00* (2006.01)
(Continued)

(52) U.S. Cl.
CPC .......... *A61B 5/1118* (2013.01); *A61B 5/0004* (2013.01); *A61B 5/1121* (2013.01);
(Continued)

(58) Field of Classification Search
CPC ... A61B 5/1118; A61B 5/0004; A61B 5/1121; A61B 5/1127; A61B 5/1128;
(Continued)

(56) References Cited

U.S. PATENT DOCUMENTS 9,078,478 B2    7/2015  Ross, Jr.
9,727,779 B2    8/2017  Utsunomiya et al.
(Continued)

FOREIGN PATENT DOCUMENTS

JP    2017023187 A    2/2017
JP    2018515298 A    6/2018
(Continued)

OTHER PUBLICATIONS

International Search Report and Written Opinion for PCT/US2019/047406, dated Nov. 27, 2019, 13 pages.

*Primary Examiner* — Michael R Bloch
*Assistant Examiner* — Nidhi N Patel
(74) *Attorney, Agent, or Firm* — Meunier Carlin & Curfman LLC

(57) ABSTRACT

A patient compliance system is provided that includes a patient monitoring material for determining movement activity associated with a joint of the patient. The patient monitoring material includes at least one sensor for sensing the movement activity and a transmitter. The system also includes a device having a receiver and a processor. The transmitter transmits the movement activity to the receiver, and the processor determines parameters associated with compliance with a rehabilitation/physical therapy program based on the movement activity. A method for monitoring movement activity of a patient is also provided. The method includes sensing movement activity associated with a joint of the patient via at least one sensor embedded within or attached to a patient monitoring material that surrounds the
(Continued)

joint; transmitting the movement activity to a device; and determining parameters associated with compliance with a rehabilitation/physical therapy program based on the movement activity via a processor.

20 Claims, 16 Drawing Sheets

(51) Int. Cl.
 *G16H 20/30* (2018.01)
 *G16H 40/67* (2018.01)
(52) U.S. Cl.
 CPC .......... *A61B 5/1128* (2013.01); *A61B 5/4833* (2013.01); *A61B 5/486* (2013.01); *A61B 5/6804* (2013.01); *A61B 5/742* (2013.01); *G16H 20/30* (2018.01); *G16H 40/67* (2018.01); *A61B 5/4571* (2013.01); *A61B 5/4576* (2013.01); *A61B 5/4585* (2013.01); *A61B 2505/09* (2013.01)
(58) Field of Classification Search
 CPC ..... A61B 5/4833; A61B 5/486; A61B 5/6804; A61B 5/742; A61B 5/4571; A61B 5/4576; A61B 5/0022; A61B 5/6828; A61B 5/6812; A61B 2505/09; G16H 20/30; G16H 40/67
 See application file for complete search history.

(56) References Cited

U.S. PATENT DOCUMENTS

| | | | |
|---|---|---|---|
| 10,551,248 | B2 | 2/2020 | Jang et al. |
| 10,709,377 | B2 | 7/2020 | Wiedenhoefer et al. |
| 2008/0161731 | A1* | 7/2008 | Woods .................. G16H 40/67 600/595 |
| 2011/0007275 | A1* | 1/2011 | Yoo ....................... A61B 5/1114 600/595 |
| 2014/0012161 | A1 | 1/2014 | Ross, Jr. |
| 2015/0324637 | A1 | 11/2015 | Utsunomiya et al. |
| 2016/0302721 | A1 | 10/2016 | Wiedenhoefer et al. |
| 2018/0106676 | A1 | 4/2018 | Jang et al. |
| 2018/0360350 | A1* | 12/2018 | Blackadar ............. G16H 20/30 |
| 2019/0066832 | A1* | 2/2019 | Kang ................... A61B 5/4884 |

FOREIGN PATENT DOCUMENTS

| | | |
|---|---|---|
| WO | WO 2016/186904 A1 | 11/2016 |
| WO | WO 2018/144712 A1 | 8/2018 |

* cited by examiner

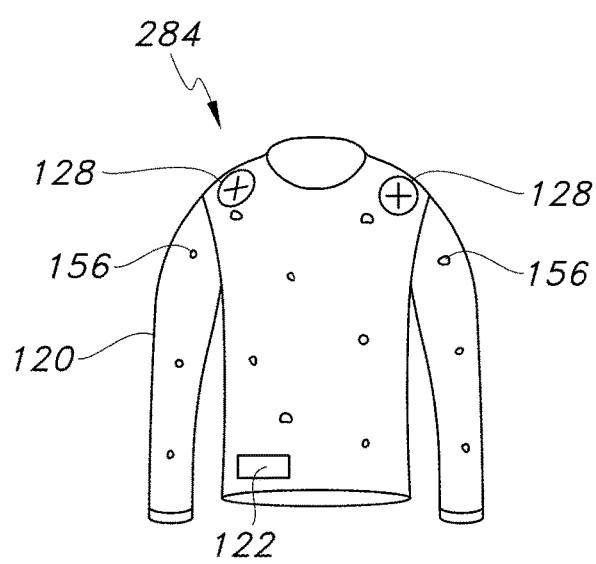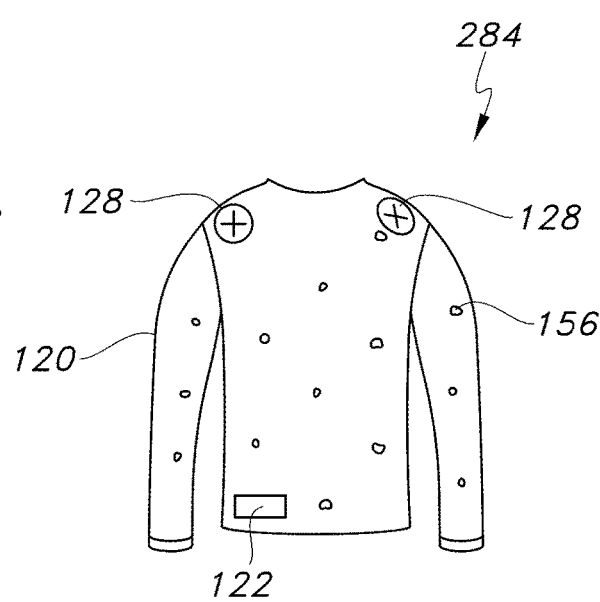
FIG. 15A  FIG. 15B
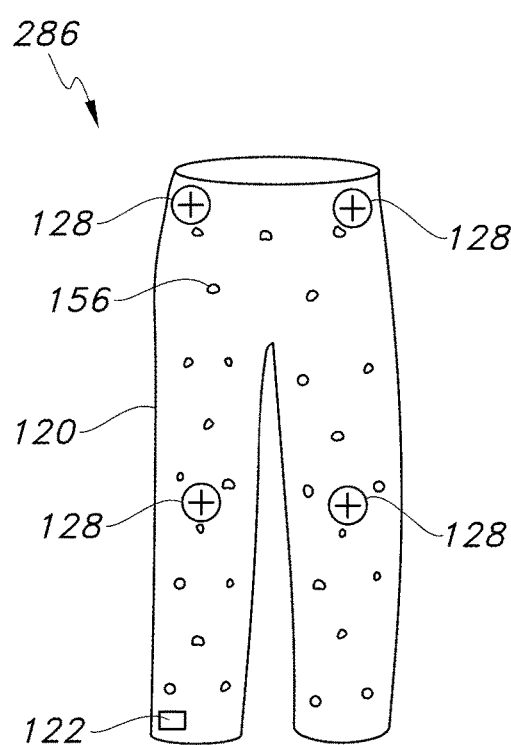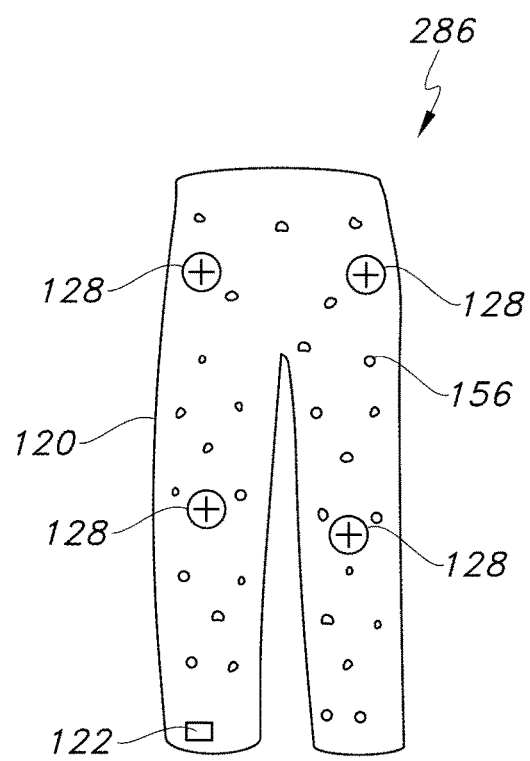
FIG. 16A  FIG. 16B

PATIENT MONITORING SYSTEM FOR DETERMINING MOVEMENT ACTIVITY

RELATED APPLICATION

The present application is the national stage entry of International Patent Application No. PCT/US2019/047406, having a filing date of Aug. 21, 2019, which claims priority to U.S. Provisional Application Ser. No. 62/724,364 entitled "Patient Monitoring System for Determining Movement Activity," filed on Aug. 29, 2018, the entire contents of which are incorporated herein in by reference.

FIELD OF THE INVENTION

The present invention relates to a patient monitoring system for determining a patient's compliance with prescribed physical therapy during rehabilitation that can optionally be used in conjunction with a patient controlled drug administration device.

BACKGROUND OF THE INVENTION

According to recent studies, there are over 600,000 total knee replacements, over 300,000 total hip replacements, over 100,000 partial hip replacements, over 25,000 partial shoulder replacements, and over 15,000 total shoulder replacements performed annually in the United States. Further, it is anticipated that by the year 2020, over 6.6 million orthopedic surgeries will be performed annually worldwide. This corresponds with over 6.6 million people ideally receiving physical therapy during a rehabilitation period post-surgery to, for instance, regain the range of motion at the surgical site, where an improved range of motion has been shown to correlate with improved patient mobility and quality of life. Although physical therapy is an important tool in the rehabilitation process, positive patient outcomes where the patient achieves an acceptable range of motion of a joint requires patient compliance in following restrictions on physical activity post-surgery and in completing at home exercises prescribed by a physical therapist between in office appointments. Unfortunately, it has been found that patient compliance in following such instructions and in completing such exercises is low.

As such, a need exists for a system that can track or monitor a patient's physical activity after an orthopedic procedure and that can provide feedback and coaching to the patient to encourage compliance with the patient's rehabilitation and physical therapy program.

SUMMARY OF THE INVENTION

In accordance with one embodiment of the present invention, a system for monitoring movement activity of a patient is provided. The system includes a patient monitoring material for determining movement activity associated with a joint of the patient, wherein the patient monitoring material includes at least one sensor for sensing the movement activity associated with the joint of the patient and a transmitter; and a device comprising a receiver and a processor, wherein the transmitter transmits the movement activity associated with the joint of the patient to the receiver, further wherein the processor determines parameters associated with compliance with a rehabilitation or physical therapy program based on the movement activity associated with the joint of the patient.

In one embodiment, the patient monitoring material can include a sleeve, one or more adhesive pads, a shirt, pants, or a combination thereof. Further, the sleeve can include a stretchable material for conforming around the joint.

In another embodiment, the joint can be a knee joint, a hip joint, or a shoulder joint.

In still another embodiment, the at least one sensor can include a dielectric elastomer accelerometer, a laser accelerometer, a low frequency accelerometer, an optical accelerometer, a piezoelectric accelerometer, a resonance accelerometer, a surface acoustic wave accelerometer, a surface micromachined capacitive accelerometer, a thermal accelerometer, a triaxial accelerometer, a potentiometric type accelerometer, a strain gauge sensor, or a combination thereof.

In yet another embodiment, the parameters associated with compliance with the rehabilitation or physical therapy program can include an angle of extension of the joint, an angle of flexion of the joint, a total number of minutes during which the patient is active over a predetermined time period, or a combination thereof.

In one more embodiment, the patient monitoring material can further include at least one reference indicator. For instance, the at least one reference indicator can be a symbol.

Moreover, the device can include an image capture mechanism configured to capture an image of the joint and can also include a display to provide information about the image. Further, the processor can display at least one reference guide on the display to assist a user in utilizing the image capture device to capture the image.

In addition, the at least one reference indicator can be capable of alignment within the at least one reference guide on the display when capturing the image, and the processor can be configured to process the image to determine an angle of extension of the joint or an angle of flexion of the joint. For instance, the image is compared to one or more stored images.

In another embodiment, the device can be wireless.

In still another embodiment, the processor can provide coaching or instructions to the patient based on the movement activity associated with the joint of the patient.

In accordance with another embodiment of the present invention, a method for monitoring movement activity of a patient is provided. The method includes sensing movement activity associated with a joint of the patient via at least one sensor embedded within or attached to a patient monitoring material, wherein the patient monitoring material surrounds the joint; transmitting the movement activity associated with the joint of the patent to a device; and determining parameters associated with compliance with a rehabilitation or physical therapy program based on the movement activity associated with the joint of the patient via a processor.

In one embodiment, the parameters associated with compliance with the rehabilitation or physical therapy program can include an angle of extension of the joint, an angle of flexion of the joint, a total number of minutes during which the patient is active over a predetermined time period, or a combination thereof.

In still another embodiment, the method can further include capturing an image of the joint via an image capture mechanism included in the device; processing the image via the processor; and displaying information to a user regarding the movement activity associated with the joint of the patient on a display.

In yet another embodiment, at least one reference guide can be displayed on the display to assist a user in capturing the image. Further, at least one reference indicator on the patient monitoring material can be aligned within the at least one reference guide when capturing the image.

Additionally, the processor can be configured to process the image to determine an angle of extension of the joint or an angle of flexion of the joint.

In one more embodiment, processing the image can include comparing the image to one or more stored images.

In an additional embodiment, the method can further include providing coaching or instructions to the patient via the device based on the movement activity associated with the joint of the patient.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE FIGURES

A full and enabling disclosure of the present invention to one skilled in the art, including the best mode thereof, is set forth more particularly in the remainder of the specification, including reference to the accompanying figures, in which:

FIG. 15A is a front view of one embodiment of the patient monitoring material of the present invention in the form of a shirt;

FIG. 15B is a rear view of one embodiment of the patient monitoring material of the present invention in the form of a shirt;

FIG. 16A is a front view of one embodiment of the patient monitoring material of the present invention in the form of a pair of pants;

FIG. 16B is a rear view of one embodiment of the patient monitoring material of the present invention in the form of a pair of pants;

Figure 1:
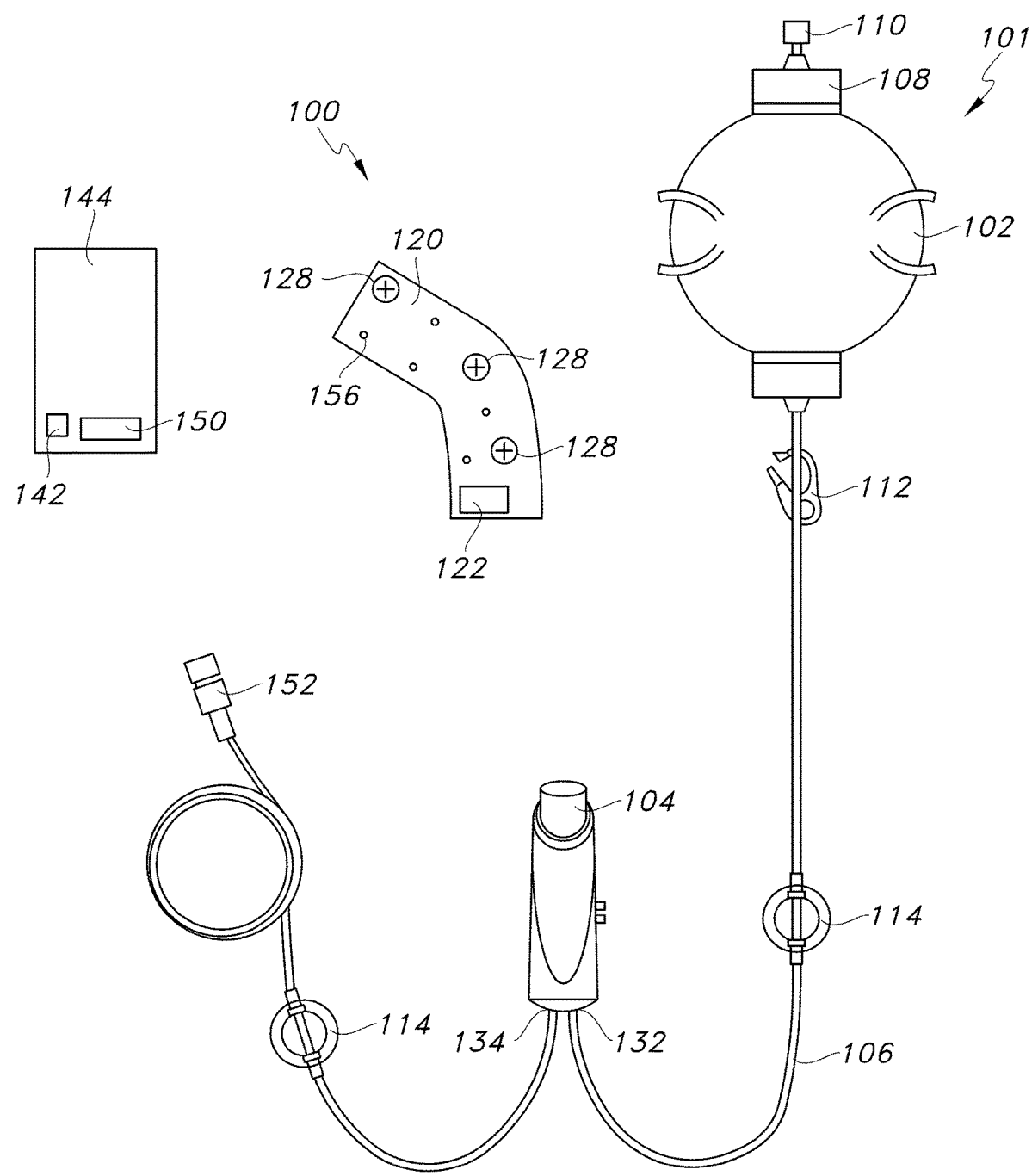
FIG. 1 illustrates a patient monitoring system of the present invention that includes a patient monitoring material and a wireless device, as well as an optional pain management device and infusion pump.

Repeat use of reference characters in the present specification and drawings is intended to represent the same or analogous features or elements of the present invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a patient monitoring system that monitors a patient's movement activity associated with a particular joint via one or more sensors present on a patient monitoring material (e.g., sleeves that fit around a joint area, adhesive pads that are attached to skin near the joint area, or clothing such as a shirt or pants that surround the joint area). The system incorporates a device (e.g., a wireless device such as a smartphone, tablet, PC, etc.) that can collect raw data from the sensors and analyze such data to convert the data to range of motion information that, in turn, can be used to track the patient's progress during rehabilitation. The patient monitoring system also includes a processor, which can be a component of the device, where the process is utilized for determining the mobility of the patient, the flexion and/or extension of the joint of the patient (e.g., knee, hip, shoulder), or any other suitable parameter for determining the patient's progress during rehabilitation after an orthopedic procedure based on the movement activity around that joint that is sensed by the one or more sensors. The patient monitoring system further includes a transmitter that can wirelessly transmit information regarding the patient's movement to the device (e.g., a wireless device such as a smartphone, tablet, PC, etc.) that can wirelessly receive the information via a receiver. Moreover, the device can optionally include an image capture mechanism that a user (e.g., the patient or a medical professional such as a physical therapist, occupational therapist, physician, etc.) can use in conjunction with one or more reference indicators that may be present on the patient monitoring material to obtain information about the patient's progress during rehabilitation. Each of these features, as well as additional features of the patient monitoring system, are discussed in more detail below.

Referring to FIG. 1, a patient monitoring system 100 is shown that includes a patient monitoring material 120 that includes one or more sensors 156 embedded therein or attached thereto in order to monitor the movement activity of a patient wearing the patient monitoring material 120. In addition, one or more reference indicators 128 can be present on the patient monitoring material 120 that can be used in conjunction with a wireless device 144 to track, for instance, a change in an angle related to the patient's range of motion at a particular joint, or any other parameter indicative of the patient's progress during rehabilitation that is desired to be tracked. Further, the patient monitoring system 100 includes a transmitter 122 embedded within or attached to the patient monitoring material and a receiver 150 and processor 142 present within the wireless device 144 for facilitating wireless communication between the patient monitoring material 120 and the wireless device 144. Such components facilitate the transmission and analysis of the data collected from the one or more sensors 156 in the patient monitoring material 120 that is ultimately sent to the wireless device 144.

Further, as also shown in FIG. 1, it is to be understood that the patient monitoring system 100 generally described above can be used in conjunction with a pain management device 101, at least for a time period immediately following the patient's surgical procedure (e.g., 3-7 days), although it is to be understood that the patient monitoring system 100 including the patient monitoring material 120 and device 144 can be used for two to three months or longer as needed. The pain management device 101 can include a drug administration device 104 and a pump 102, which can be filled with a liquid drug (e.g. an analgesic) via fill port 108 by removing fill cap 110. The pump 102 can be connected to the drug administration device 104 via tubing 106 at an inlet conduit 132. A clamp 112 can be used to control the flow of the drug from the liquid pump 102 to the drug administration device 104 as needed. An air eliminating filter 114 can also be utilized in the pain management device 101. The drug administration device 104 can also include an outlet conduit 134, where tubing 106 extends from the outlet conduit 134 to a patient's catheter (not shown) by removing luer fitting 152 so that the patient can receive the liquid drug. The pump 102 can provide continuous infusion (basal) of the liquid drug, while the drug administration device 104 can allow for the delivery of a fixed bolus of the liquid drug, where the delivery is "on demand" as needed by the patient or healthcare provider. Further, although not shown, it is to be understood that, in some embodiments, the pain management device 101 can communicate wirelessly with the wireless device 144 such that delivery of the liquid drug can be controlled via the wireless device 144. Specific features of the various components of the patient monitoring system 100 and the areas of the body (e.g., joints) in which the patient monitoring system 100 can be used to monitor a patient's movement activity will now be discussed in more detail with respect to FIGS. 2-19.

Figure 2:
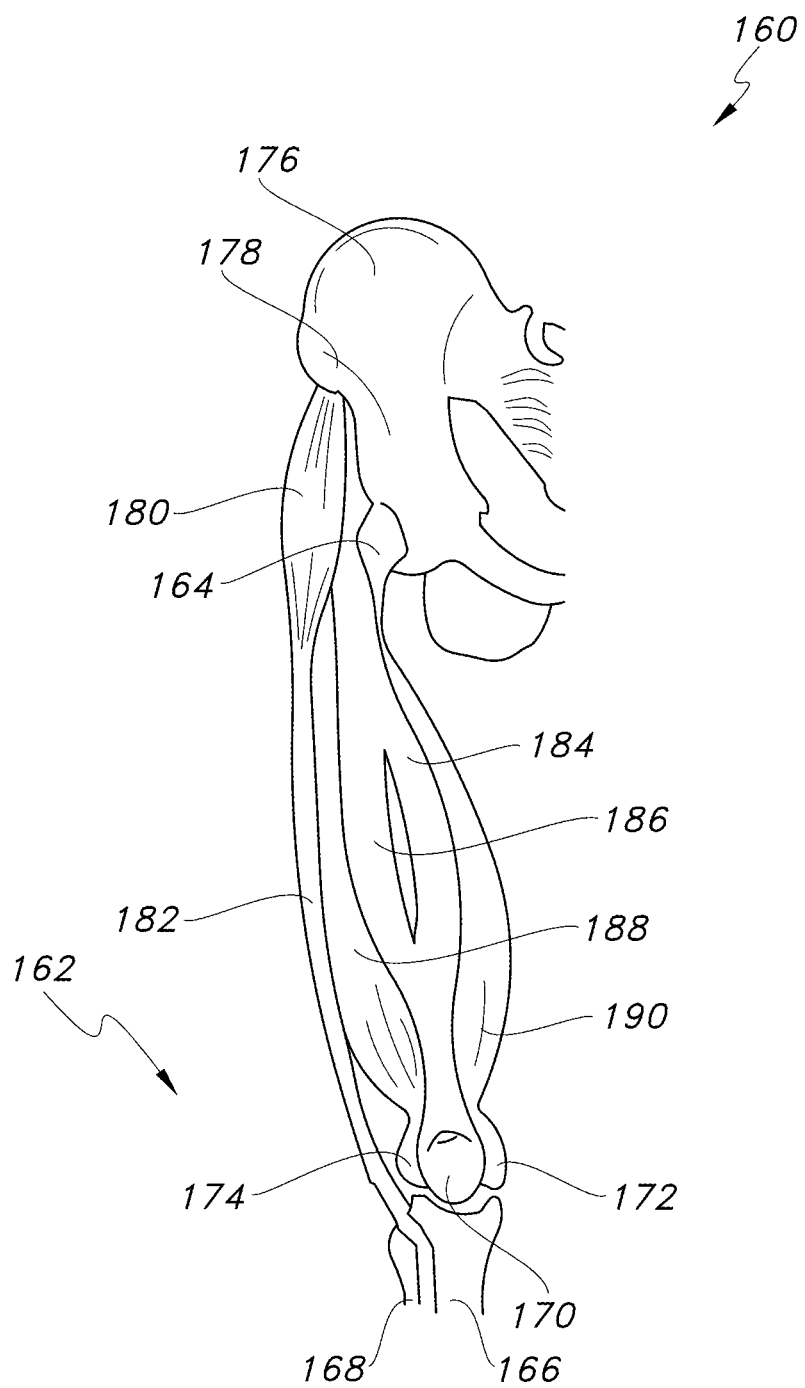
FIG. 2 is an anterior view of a leg of a patient showing the bones and muscles around the knee joint that can be monitored by the patient monitoring system of the present invention.

Referring first to FIG. 2, an anterior view of a leg 160 of a patient showing the muscles around the knee joint 162 where the medial condyle 172 of the femur 164, the lateral condyle 174 of the femur 164, the patella 170, the tibia 166, and the fibula 168 meet and that can be monitored by the patient monitoring system 100 of the present invention is provided. For example, muscles that can be monitored include the tensor fascia latae muscle 180 that originates at the anterior superior iliac spine 178 of the ilium 176 and is reinforced by the iliotibial (IT) band 182, the rectus femoris muscle 184, the vastus intermedius muscle 186, the vastus lateralis muscle 188, the vastus medialis muscle 190, although it is to be understood that any other muscles in the area of the knee joint 162 can also be monitored.

Figure 3:
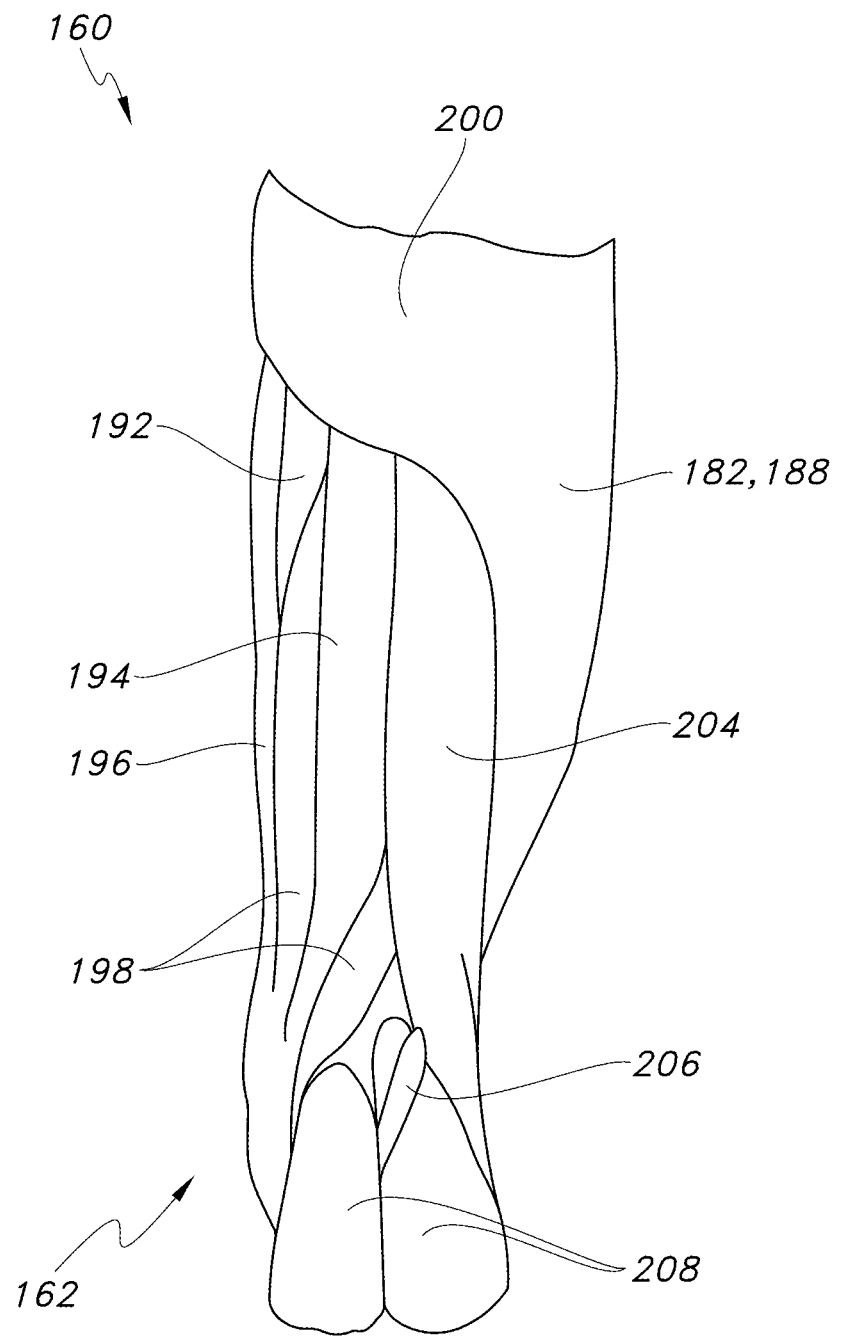
FIG. 3 is a posterior view of a leg of a patient showing the muscles around the knee joint that can be monitored by the patient monitoring system of the present invention.

Next, referring to FIG. 3, a posterior view of a leg 160 of a patient showing the muscles around the knee joint 162 that can be monitored by the patient monitoring system 100 of the present invention is provided. For example, muscles that can be monitored include the adductor magnus muscle 192, the semitendinosus muscle 194, the semimembranosus muscle 198, the biceps femoris muscle 204, the gracilis muscle 196, the gastrocnemius muscle 208, the plantaris muscle 206, the gluteus maximus muscle 200, and the vastus lateralis muscle 188 adjacent the IT band 182, although it is to be understood that any other muscles in the area of the knee joint 162 can also be monitored.

Specifically, when a patient has undergone a knee-related surgery such as a total knee replacement, the patient monitoring system 100 of the present invention can be used to monitor movement activity associated with the muscles described above in FIGS. 2-3 and then determine if a patient is complying with his or her prescribed rehabilitation program, determine the range of flexion and/or extension of the knee joint 162, and/or provide additional coaching or feedback, etc. based on analysis of the movement activity.

Figure 4:
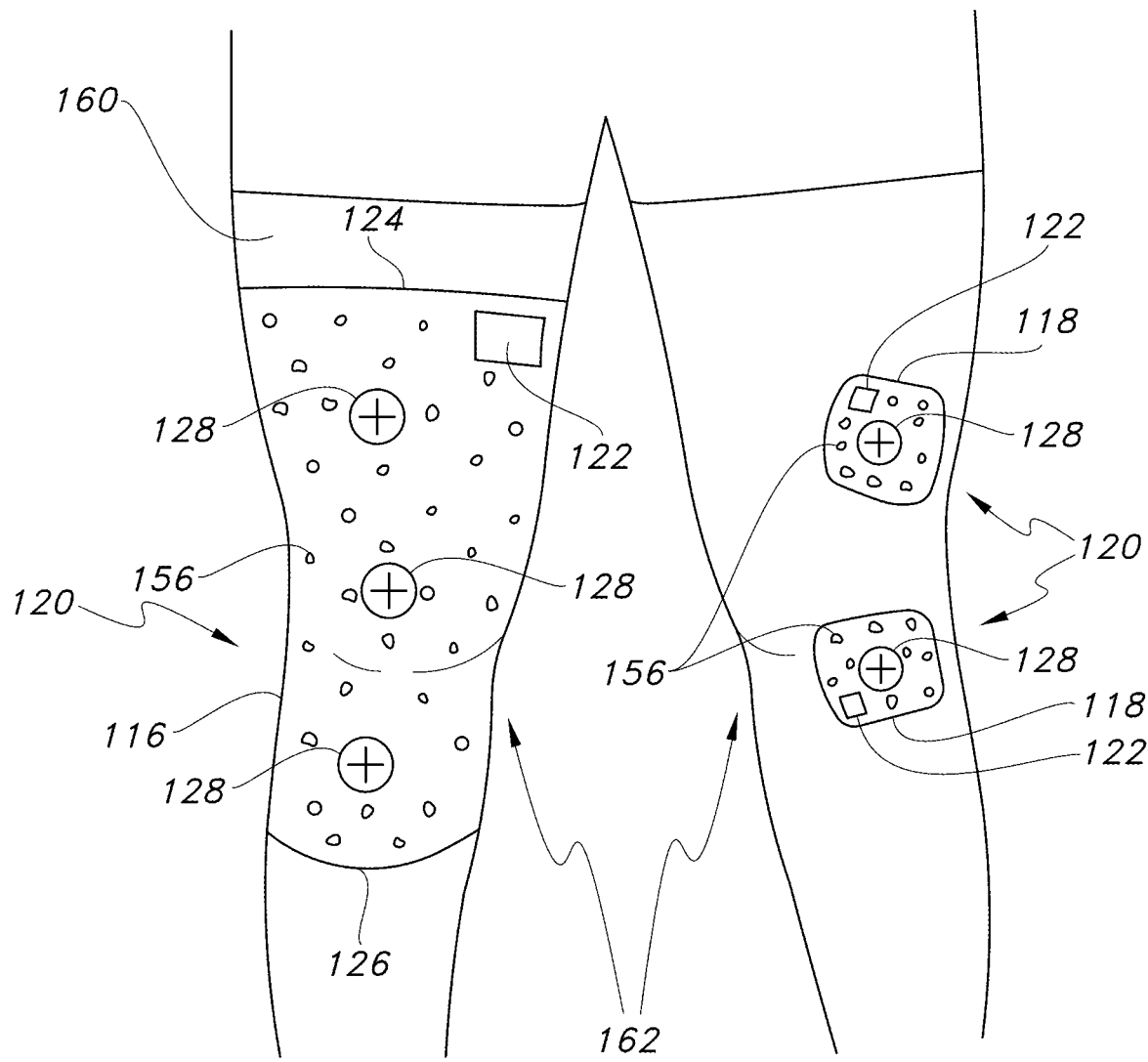
FIG. 4 is a front view of a right knee joint and a left knee joint of a patient, where the patient is wearing the patient monitoring material of the present invention in the form of a sleeve on the right knee and in the form of multiple adhesive pads on the left knee.

Turning now to FIG. 4, a front view of the right and left knee joints 162 of a patient, where the patient is wearing the patient monitoring material 120 of the present invention in the form of a sleeve 116 having a proximal end 124 and a distal end 126 on the right knee and in the form of multiple adhesive pads 118 on the left knee is shown. The sleeve 116 can be formed from any suitable woven or non-woven fabric, such as a stretchable fabric that can conform to the shape of the particular joint of the patient around which the sleeve 116 is worn. Meanwhile, the adhesive pads 118 can also be formed from any suitable woven or nonwoven fabric or a polymeric film-like material, where a body-facing surface of the adhesive pads 118 includes an adhesive layer (e.g., double-sided tape, pressure sensitive adhesive, etc.) for attaching the adhesive pads 118 to the patient.

Figure 5:
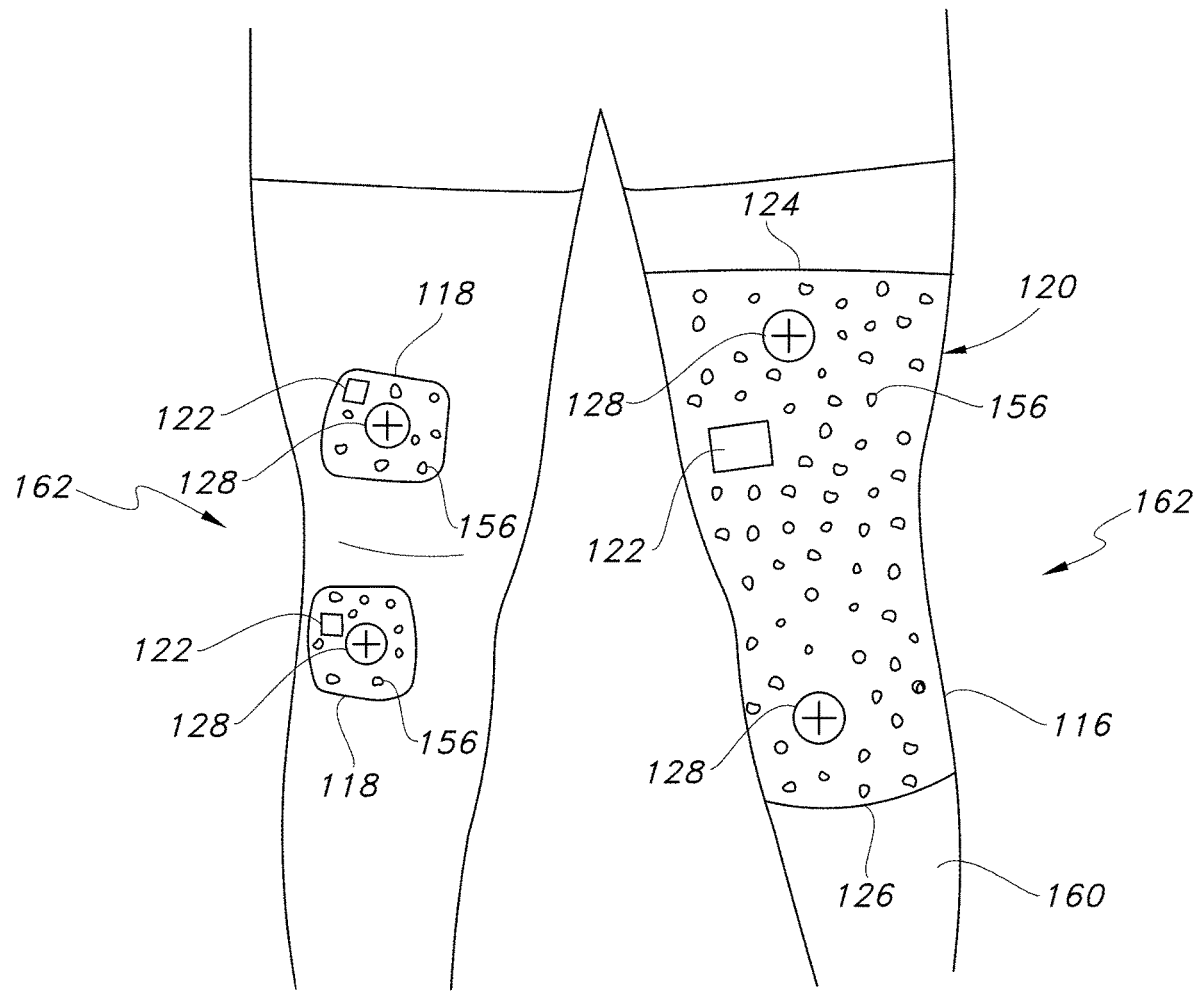
FIG. 5 is a rear view of a right knee joint and a left knee joint of a patient, where the patient is wearing the patient monitoring material of the present invention in the form of a sleeve on the right knee and in the form of multiple adhesive pads on the left knee.
Figure 6:
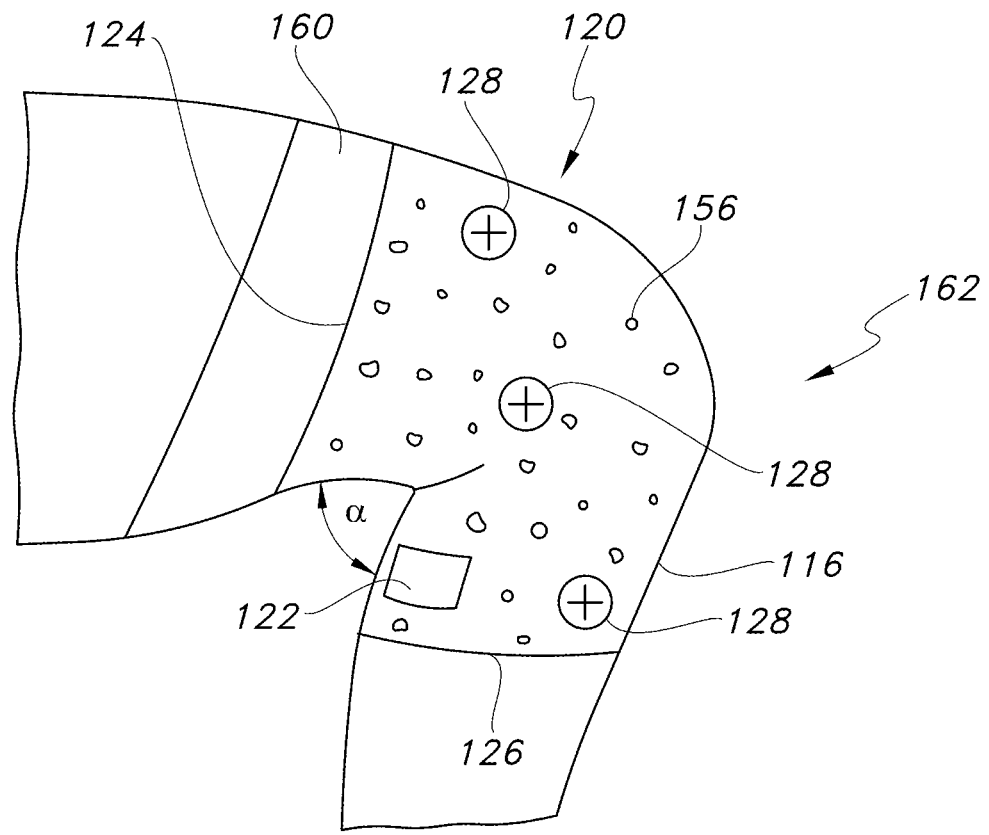
FIG. 6 is a side view, either lateral or medial, of a knee joint of a patient while the knee joint is bent and where the patient is wearing the patient monitoring material of the present invention in the form of a sleeve.

Referring now to FIG. 5, a rear view of a right and left knee joints 162, where the patient is wearing the patient monitoring material 120 of the present invention in the form of a sleeve 116 having a proximal end 124 and a distal end 126 on the right knee and in the form of multiple adhesive pads 118 on the left knee is shown. Further FIG. 6 shows a side view of a knee joint 162 of a patient while the leg 160 is bent or flexed, where the patient is wearing the patient monitoring material 120 of the present invention in the form of a sleeve 116, although it is to be understood that one or more adhesive pads 118 can be used instead of or in conjunction with the sleeve 116.

In any event, regardless of whether a sleeve 116 or adhesive pads 118 are utilized as the patient monitoring material 120, the patient monitoring material 120 can be used to monitor the movement activity of the muscles near the knee joint 162 described above with respect to FIGS. 2-3. Specifically, as shown in FIGS. 4-6, one or more sensors 156 can be embedded within or attached to the patient monitoring material 120 to detect and measure the movement activity of the patient, which can be communicated to a wireless device 144 via a transmitter 122. Although any suitable sensor can be used, in one particular embodiment, the one or more sensors 156 can be a motion sensor such as an accelerometer. Further, one or more sensors 156 can include a dielectric elastomer accelerometer, a laser accelerometer, a low frequency accelerometer, an optical accelerometer, a piezoelectric accelerometer, a resonance accelerometer, a surface acoustic wave accelerometer, a surface micromachined capacitive accelerometer, a thermal accelerometer, a triaxial accelerometer, a potentiometric type accelerometer, a strain gauge sensor (e.g., a mechanical, optical, acoustical electrical, metallic wire, foil, film, thin-film, or semiconductor strain gauge sensor), or a combination thereof. In one particular embodiment, the sensor 156 can be a strain gauge sensor, where the strain measured from the medial femoral condyle 172 under the vastus medialis muscle 190 can be directly correlated to, for instance, knee joint 162 flexion and/or extension, although it is to be understood that the strain or any other bone or muscles in a particular joint can also be correlated to joint mobility and range of motion (e.g., flexion and/or extension).

The patient monitoring material 120 can also include a processor 142 for determining a range flexion and/or extension of the knee joint 162 (or any other joint near which the patient monitoring material 120 is placed, such as the hip joint 210 and/or the shoulder joint 240 as shown in FIGS. 7-14), and for determining if a patient is complying with his or her prescribed rehabilitation program based on the movement activity sensed by the sensors 156. More specifically, the processor 142, which can be a component of the wireless device 144, may compare the patient's level of movement activity as sensed by the one or more sensors 156 to a baseline level of movement activity to determine if the patient is taking part in too much or too little physical activity compared to a baseline level of movement activity for the particular point in the patient's rehabilitation program. Further, the processor 142 can determine an angle α of extension (not shown) or flexion (see FIG. 6) of a joint to determine if the patient's range of motion is decreased or increased compared to a baseline level of extension or flexion for the particular point in the patient's rehabilitation program. Further, the one or more sensors 156 can be tied to specific anatomical references (e.g., a particular muscle, bone, etc.) to provide spatial coordinates to the processor 142 so that the processor 142 can determine the patient's range of motion. In addition, based on such movement activity and range of motion information, the processor 142 can instruct the system 100 to provide additional coaching or feedback to the patient to encourage the patient as needed during the rehabilitation process to improve compliance with the prescribed physical therapy program.

The patient monitoring material 120 can also include one or more reference indicators 128 that can be used in conjunction with a wireless device 144 to track, for instance, a change in an angle α related to the patient's range of motion at a particular joint, or any other parameter indicative of the patient's progress during rehabilitation that is desired to be tracked, as will be discussed in more detail with reference to FIGS. 17A and 17B and 18.

Figure 7:
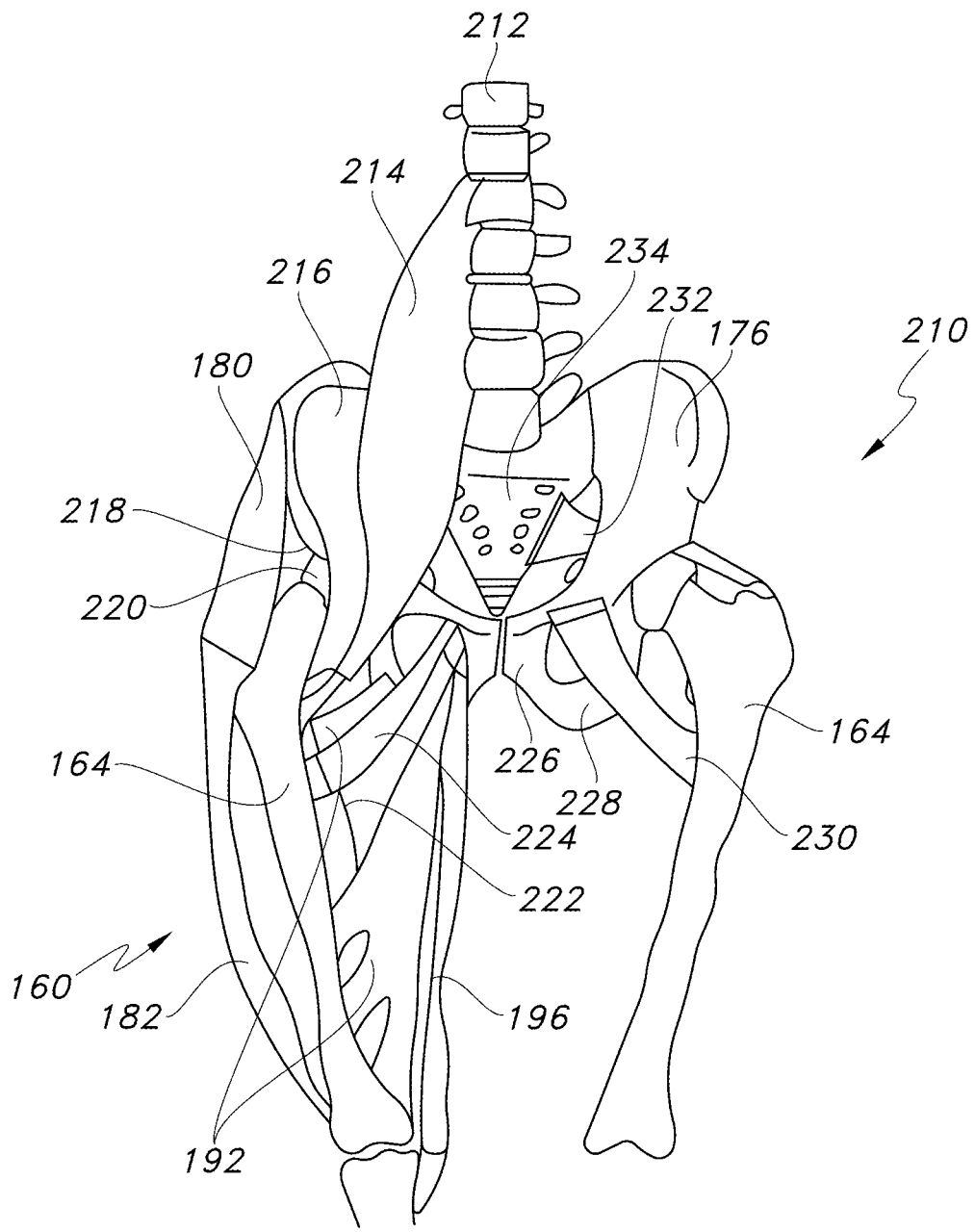
FIG. 7 is an anterior view of the hips of a patient showing the bones and muscles around the hip joint that can be monitored by the patient monitoring system of the present invention.

Turning now to FIG. 7, an anterior view of the hips of a patient showing the bones and muscles around the hip joint 210 where the femoral head 220 of the femur 164 meets the acetabulum 218 lateral and distal to the spine 212, distal to the ilium 176, lateral to the sacrum 234, and proximal and lateral to the pubis 226 and ischium 228 and that can be monitored by the patient monitoring system 100 of the present invention is provided. For example, muscles that can be monitored include the psoas major muscle 214, the iliacus muscle 216, the tensor fascia latae muscle 180, the adductor mangus muscle 192, the adductor longus muscle 222, the adductor brevis muscle 224, the gracilis muscle 196, the pectineus muscle 230, and the piriformis muscle 232, although it is to be understood that any other muscles in the area of the hip joint 210 can also be monitored.

Figure 8:
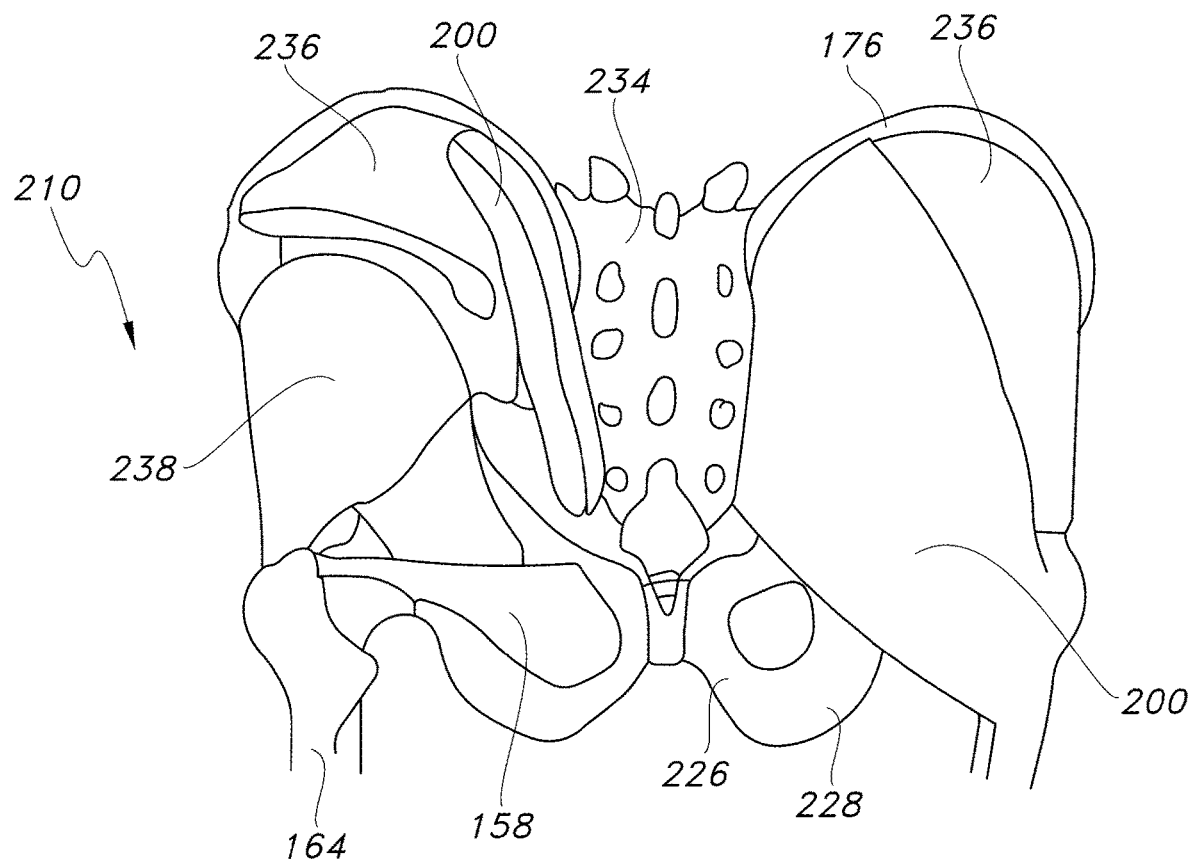
FIG. 8 is a posterior view of the hips of a patient showing the bones and muscles around the hip joint that can be monitored by the patient monitoring system of the present invention.

Referring to FIG. 8, a posterior view of the hips of a patient showing the bones and muscles around the hip joint 210 that can be monitored by the patient monitoring system 100 of the present invention is provided. For example, muscles that can be monitored include the gluteus maximus muscle 200, the gluteus medius muscle 236, the gluteus minimus muscle 238, and the obturator internus muscle 158, although it is to be understood that any other muscles in the area of the hip joint 210 can also be monitored.

Figure 9:
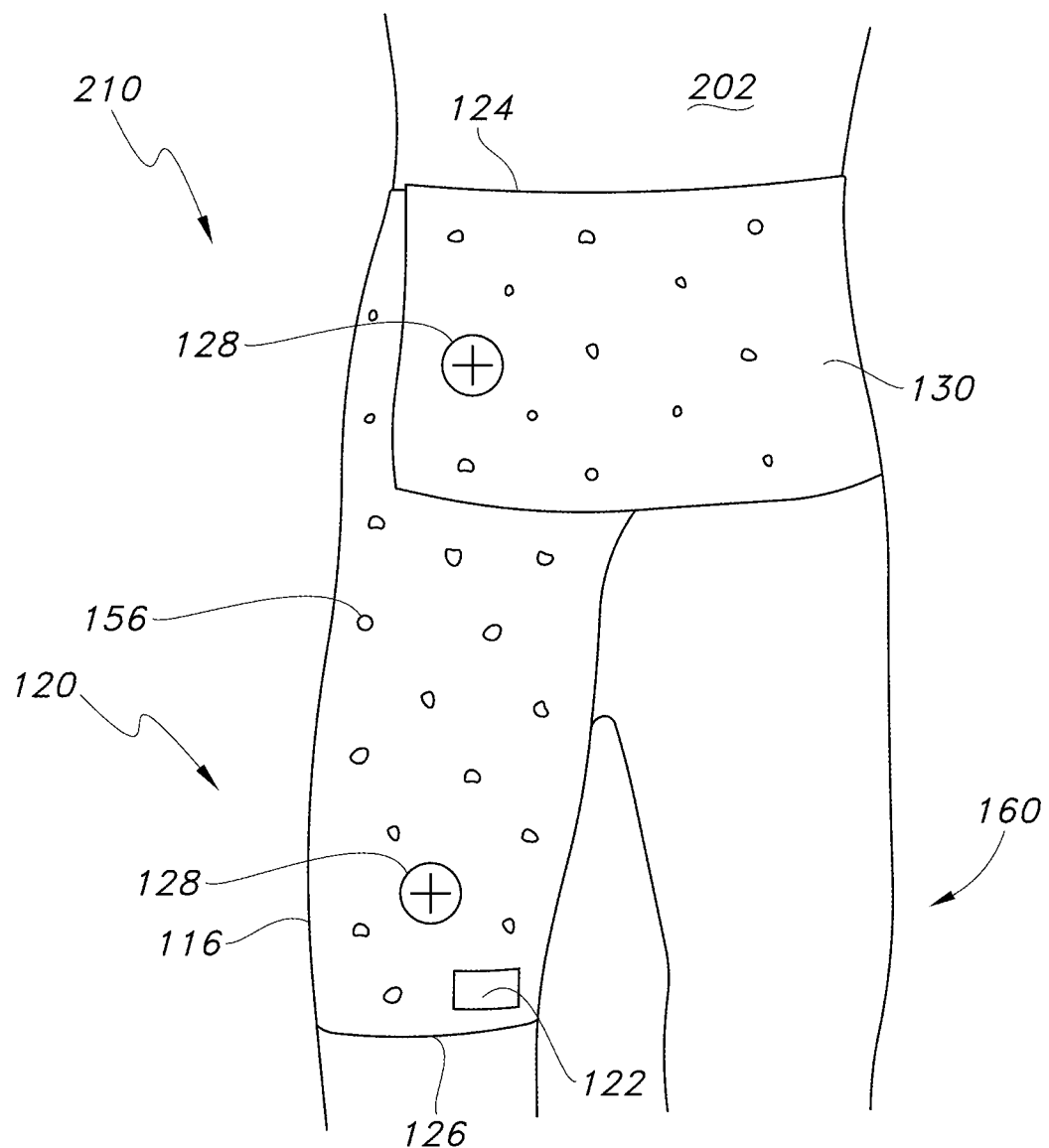
FIG. 9 is a front view of a patient from the waist area to the knee, where the patient is wearing the patient monitoring material of the present invention in the form of a sleeve on the right hip.
Figure 10:
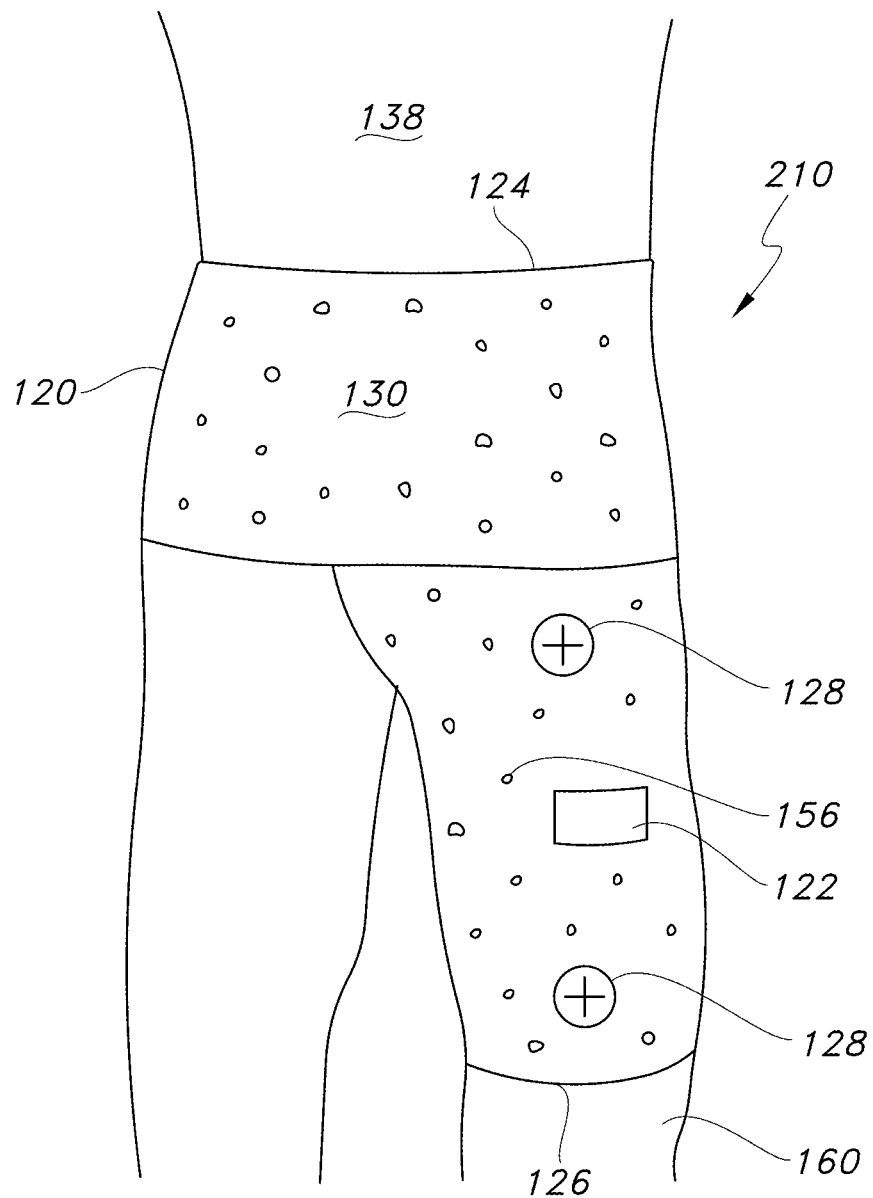
FIG. 10 is a rear view of a patient from the waist area to the knee, where the patient is wearing the patient monitoring material of the present invention in the form of a sleeve on the right hip.

Turning now to FIG. 9 is a front view of a patient from the waist area or abdomen 202 to the leg 160 just above the knee, where the patient is wearing the patient monitoring material 120 of the present invention in the form of a sleeve 116 on the right hip, although it is to be understood that a sleeve 116 can additionally or alternatively be present on the left hip, or adhesive pads 118 as described above with respect to FIGS. 4-5 can be used instead of a sleeve 116. Meanwhile, FIG. 10 is a rear view of a patient from the waist area or back 138 to the leg 160 just above the knee, where the patient is wearing the patient monitoring material 120 of the present invention in the form of a sleeve 116 on the right hip although it is to be understood that a sleeve 116 can additionally or alternatively be present on the left hip, or adhesive pads 118 as described above with respect to FIGS. 4-5 can be used instead of a sleeve 116. The patient monitoring material 120 in the form of a sleeve 116 includes a proximal end 124 and a distal end 126. In addition, the patient monitoring material 120 can include a band 130 for securing the fit of the sleeve 116 about the patient's waist area or abdomen 202. Further, the patient monitoring material 120 includes one or more sensors 156 as well as a transmitter 122 and can further include one or more reference indicators 128 as described above with respect to FIGS. 5-6 and as will be discussed in more detail reference to FIGS. 17A and 17B and 18.

Figure 11:
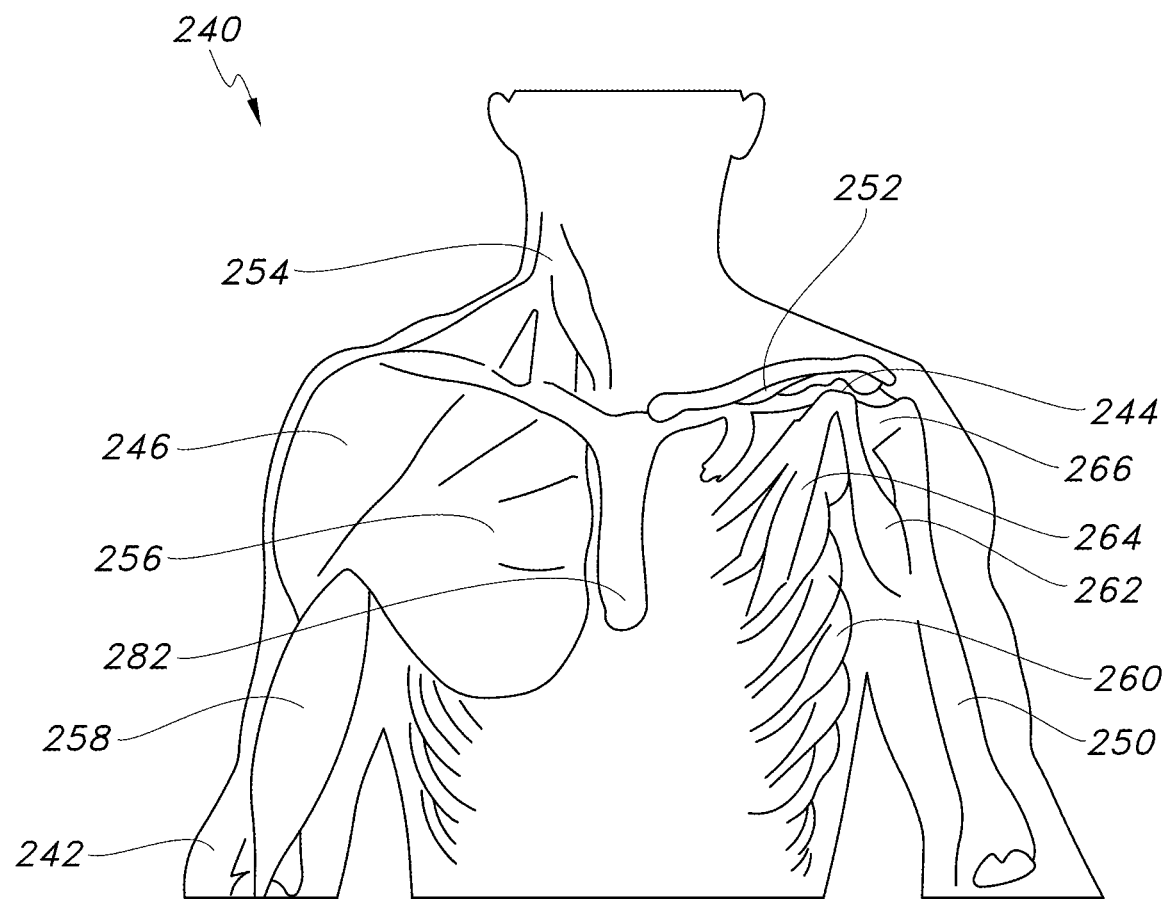
FIG. 11 is an anterior view of the shoulders of a patient showing the bones and muscles around the shoulder joint that can be monitored by the patient monitoring system of the present invention.

Referring now to FIG. 11, an anterior view of the shoulders of a patient showing the bones and muscles around the shoulder joint 240 where the humerus 250 of the arm 242 and the scapula 248 (see FIG. 12) meet that can be monitored by the patient monitoring system 100 of the present invention is provided. For example, the muscles that can be monitored include the deltoid muscle 246 and the subclavius muscle 252, which are both connected to the clavicle 244, the sternocleidomastoid muscle 254, which originates at the sternum 282 and the clavicle 244, the pectoralis major muscle 256, the biceps brachii muscle 258, the serratus anterior muscle 260, the coracobrachialis muscle 262, the pectoralis minor muscle 264, and the subscapularis muscle 266 although it is to be understood that any other muscles in the area of the shoulder joint 240 can also be monitored.

Figure 12:
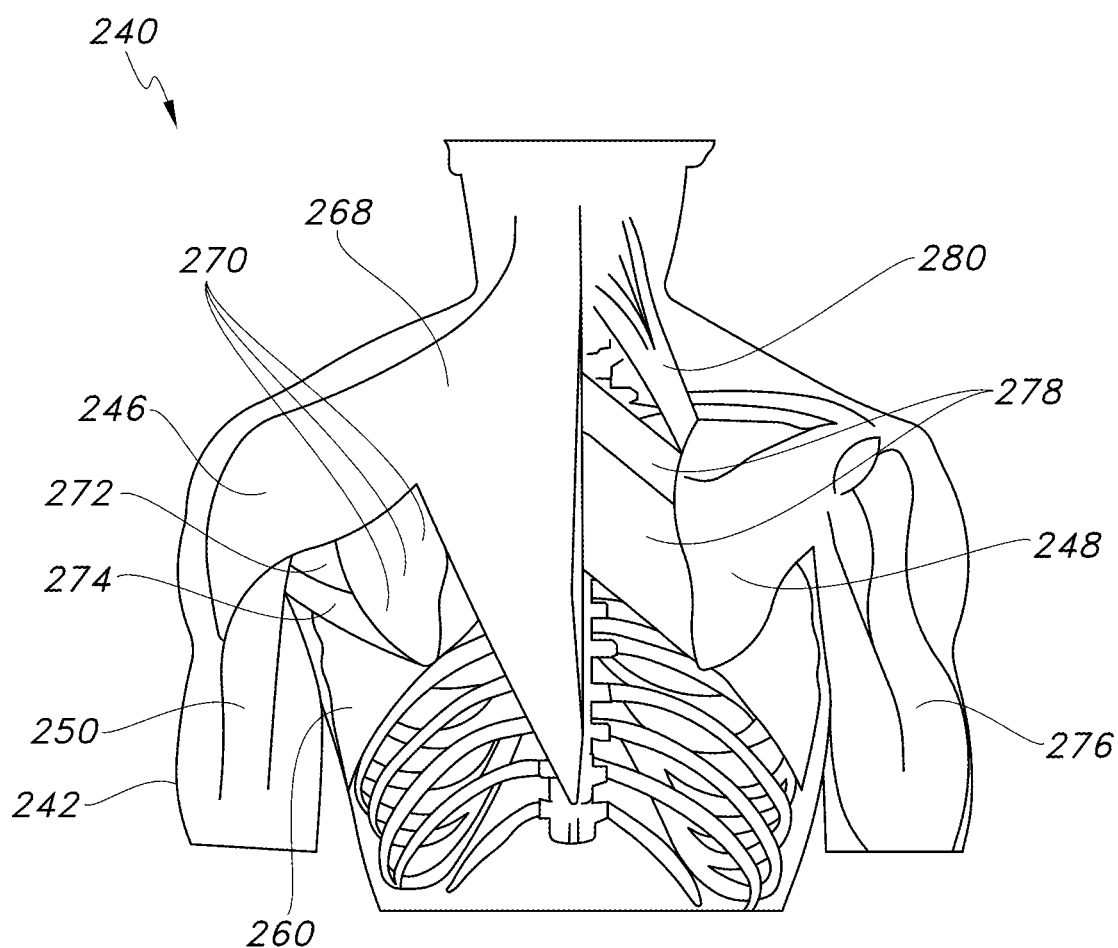
FIG. 12 is a posterior view of the shoulders of a patient showing the bones and muscles around the shoulder joint that can be monitored by the patient monitoring system of the present invention.

Next and turning to FIG. 12, a posterior view of the shoulders of a patient showing the bones and muscles around the shoulder joint 240 that can be monitored by the patient monitoring system 100 of the present invention is provided. For example, muscles that can be monitored include the trapezius muscle 268, the deltoid muscle 246, the infraspinatus muscle 270, the teres minor muscle 272, the teres major muscle 274, the triceps brachii muscle 276, the rhomboid muscles 278, and the levator scapulae muscle 280, although it is to be understood that any other muscles in the area of the shoulder joint 240 can also be monitored.

Figure 13:
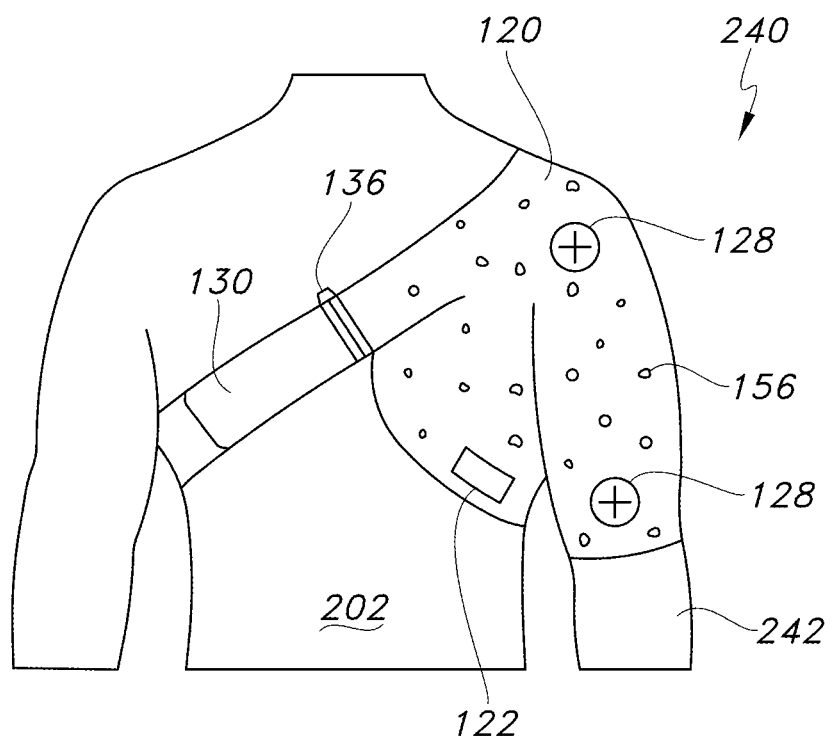
FIG. 13 is a front view of a patient from the neck area to the waist area, where the patient is wearing the patient monitoring material of the present invention in the form of a sleeve on the left shoulder.
Figure 14:
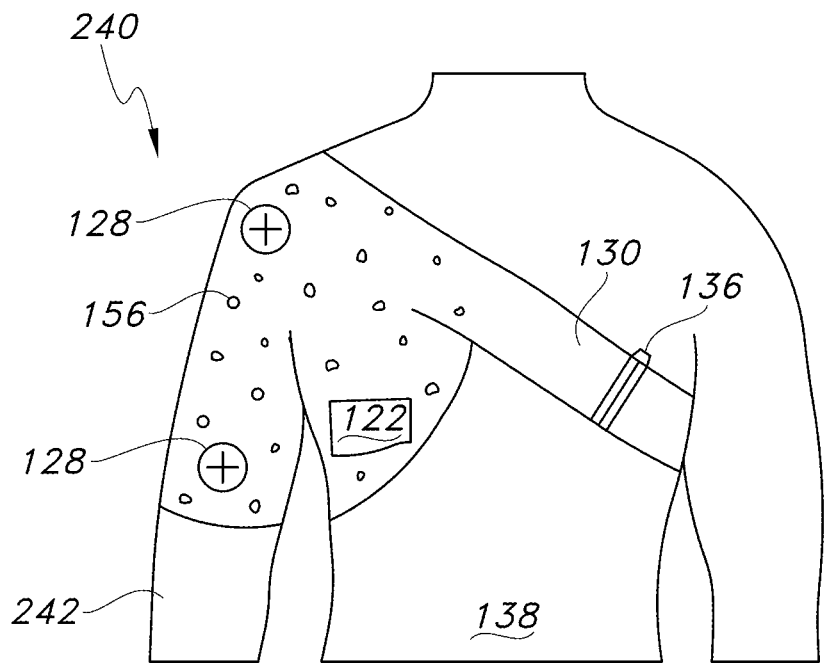
FIG. 14 is a rear view of a patient from the neck area to the waist area, where the patient is wearing the patient monitoring material of the present invention in the form of a sleeve on the left shoulder.

FIG. 13 is a front view of a patient from the neck area to the waist area or abdomen 202, where the patient is wearing the patient monitoring material 120 of the present invention in the form of a sleeve 116 on the left shoulder extending down the patient's arm 242, although it is to be understood that a sleeve 116 can additionally or alternatively be present on the right shoulder, or adhesive pads 118 as described above with respect to FIGS. 4-5 can be used instead of a sleeve 116. Meanwhile, FIG. 14 is a rear view of a patient from the neck area to the waist area or back 138, where the patient is wearing the patient monitoring material of the present invention in the form of a sleeve on the left shoulder extending down the patient's arm 242, although it is to be understood that a sleeve 116 can additionally or alternatively be present on the right shoulder, or adhesive pads 118 as described above with respect to FIGS. 4-5 can be used instead of a sleeve 116. The patient monitoring material 120 in the form of a sleeve 116 includes a proximal end 124 and a distal end 126. In addition, the patient monitoring material 120 can include a band 130 for securing the fit of the sleeve 116 around the patient's midsection above the abdomen 202 and back 238, where the band 130 can be tightened or loosened via adjustment clip 136. Further, the patient monitoring material 120 includes one or more sensors 156 as well as a transmitter 122 and can further include one or more reference indicators 128 as described above with respect to FIGS. 5-6 and as will be discussed in more detail reference to FIGS. 17A and 17B and 18.

Specifically, an image capture mechanism 140 and a processor 142 contained within the wireless device 144 may be used in conjunction with the patient monitoring material 120 as part of the patient monitoring system 100 of the present invention. The image capture mechanism 140 and the processor 142 can allow a user (e.g., the patient or a medical professional) to receive a plurality of information gleaned from the patient monitoring material 120 to determine the level of movement activity of the patient, to determine the amount of extension and/or flexion of a joint (e.g., knee, hip, shoulder, etc.), and/or to determine whether or not a patient is complying with his or her prescribed rehabilitation program, determine a range flexion and/or extension of the knee joint 162, where such information can then be used to provide coaching or feedback to the patient.

Figure 17A:
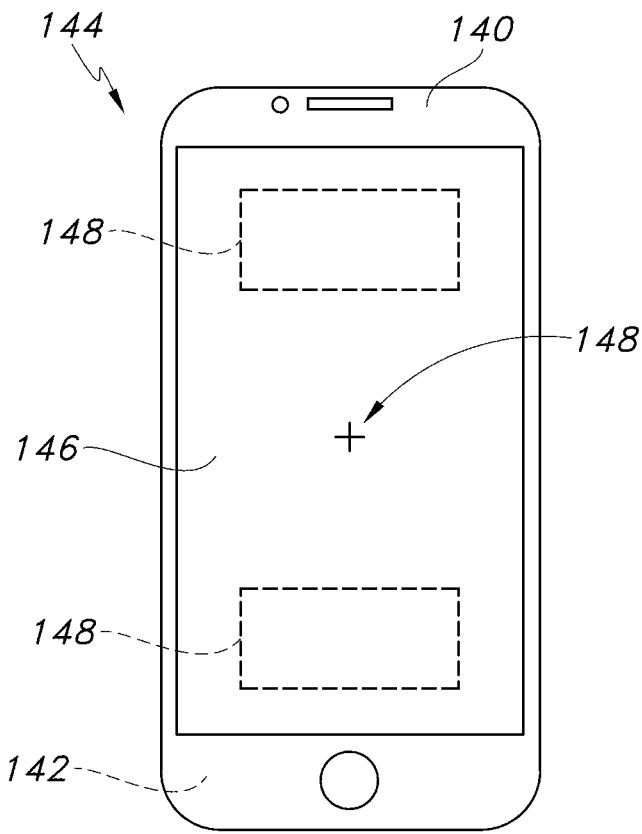
FIG. 17A is a front view of the wireless device of FIG. 1 having a display according to one embodiment of the present invention.
Figure 17B:
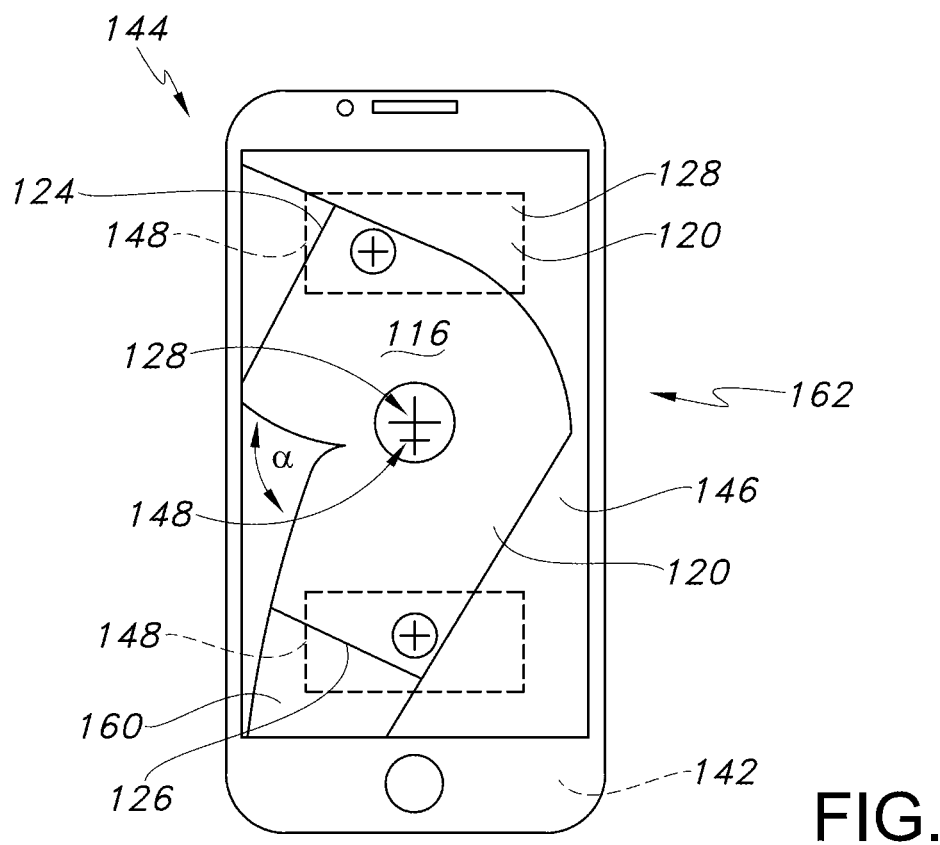
FIG. 17B is a front view of the wireless device of FIG. 2A showing the patient monitoring material aligned with guides on the display, according to one embodiment of the present invention.

In the embodiment shown in FIGS. 17A and 17B, the image capture mechanism 140 and processing system 142 are incorporated into a single device, which can be a wireless device 144 (e.g., a wireless smartphone, tablet, or PC) having a display 146. Utilizing, for instance, the image capture mechanism 140 of the wireless device 144 and display 146, a user may capture an image (i.e., take a picture) of a patient's joint (e.g., knee, hip, shoulder, etc.), and the processor 142 contained within the wireless device 144 may then deliver one or more pieces of information regarding the movement activity associated with the joint.

For example, as shown in FIGS. 17A and 17B, the processor 142 may utilize a software application or app that helps the user capture the image of particular area of interest of a particular joint (e.g., knee, hip, shoulder, etc.) displaying one or more guides 148. For illustrative purposes, a knee joint 162 is utilized in FIG. 17B, although it is to be understood that an image can be captured of any other desired joint in a similar manner as described herein. In particular, the user may open or activate the app on the user's wireless device 144 (e.g., a smartphone, a tablet, a PC, etc.). Next, such as upon selection of a particular mode or feature, the app may display one or more reference guides 148 on the display 146. The user may then utilize the reference guides 148 to position the knee joint 162 within a field of view of the image capture mechanism 140 of the wireless device 144. The reference guides 148 may, e.g., help the user capture an image of the knee joint 162 containing relevant features of the patient monitoring material 120 needed for the processor 142 to determine relevant information as to the movement activity of a patient (e.g., an angle α of flexion of the knee joint 162, or the angle of flexion and/or extension of any other desired joint), such as a reference indicator 128. For example, if the user does not capture the proximal end 124 and distal end 126 of the sleeve 116, the processor 142 may be unable to determine that it has a useable image for accurately assessing the movement activity of the patient. Thus, the reference guides 148 may help ensure the user captures a useful image of the sleeve 116 (or adhesive pads 118, shirt 284, pants 286, or any other suitable patient monitoring material) by providing a window within which to align one or more reference indicators 128 on the patient monitoring material 120.

Further, while FIG. 17B depicts capturing an image of the patient monitoring material 120 extending between a proximal end 124 and a distal end 126, in some embodiments the user need not capture the proximal end 124 and the distal end 126 of the patient monitoring material 120. Nevertheless, in embodiments in which the reference indicator 128 may be used to determine an angle α of flexion or extension of a joint, it will be appreciated that it may be helpful to capture a static, i.e., unchanging, portion of the patient monitoring material 120 in which the particular joint of interest is neither flexed nor extended for comparing successive images of the patient monitoring material. As shown, the one or more reference indicators 128 can be in the form of a plus (+) sign contained within a circle, but it should be understood that the reference indicators 128 may have other forms, shapes, or configurations in other embodiments (e.g., a star, a square, an asterisk, a circle, etc.).

In addition, it is to be understood that a reference indicator 128 is capable of alignment within at least one of the reference guides 148 on the display 146 when capturing the image. Then the processor 142 can determine an angle of extension or an angle of flexion of the joint based on the captured image, such as by comparing the captured image to one or more stored images, where each image is associated with a particular angle of extension or an angle of flexion. Thus, based on the image captured by the user, processor 142 may calculate the angle α of flexion or extension of a particular joint at the time that the user captured the image and display the angle information to the user via the display 146 of the wireless device 144. The processor 142 also may display other information on the display 146, such as the movement activity of the patient based on data collected from sensors 156. Further, in some embodiments, the processor 142 may prompt the user, e.g., via a visual and/or audible signal of the wireless device 144, to capture images of the particular joint of interest and the patient monitoring material 120 surrounding the joint at various time intervals. Capturing images over time may help the processor 142 to provide more information and/or more accurate information regarding the movement activity of the patient. As an example, comparing multiple images of a particular joint over a time interval may allow the processor 142 to determine if the angle α of flexion or extension of a particular joint is increasing, staying constant, or decreasing, where an increase in the angle α of flexion or extension can correspond with an increased range of motion and mobility for the patient, which can be indicative of compliance with a prescribed at-home rehabilitation program. On the other hand, no change or a decrease in the angle α of flexion or extension can correspond with a decreased range of motion and mobility for the patient, which can be indicative of compliance with a prescribed at-home rehabilitation program. Further, the processor 142 may be configured to store each captured image such that the images may be compared to one another as well as each newly captured image.

Accordingly, the display 146 may provide a visual indication of the movement activity, range of motion, and mobility of patient wearing the patient monitoring material 120 of the present invention. For example, the display 146 may provide a graphical representation of the change in the angle α of flexion or extension. Alternatively or additionally, the display 146 may provide a graphical representation of the number of active minutes over a predetermined time period as determined from the motion sensors 156. In other embodiments, the display 146 may provide a numerical indication of the change in the angle α of flexion or extension or the number of active minutes over a predetermined time period. The display 146 may indicate other conditions or provide other information as well.

Further, the processor 142 may assimilate data provided from one or more sources, such as the image capture mechanism 140 and software application of the wireless device 144 as described above and/or input(s) from a medical professional and/or patient. Then, the processor 142 may display such data or information derived from such data to the medical professional or patient, such as by using the display 146 of the wireless device 144. For example, as shown schematically in FIG. 18, data or information from the patient monitoring system 100, including the patient monitoring material 120, may be sent to and/or captured by one or more patient or user wireless devices 144 linked to a network 302 (e.g., over or through a communications network 302 or via a wireless relay or module). Wireless devices 144 can include, for example, a personal computing device, such as portable or wireless mobile telecommunications devices with Internet functionality, such as a smartphone. As further examples, wireless devices 144 may be tablet computers, or any other suitable personal computing devices. It is also to be understood that in some embodiments, a desktop computer that may or may not be wireless is contemplated. In some embodiments, each wireless device 144 includes a control circuit having one or more processors and an associated memory device configured to perform a variety of computer-implemented functions (e.g., performing the methods, steps, calculations and the like described herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements.

Such memory device(s) may generally be configured to store suitable computer-readable instructions that, when implemented by the processor(s), configure the control circuit to perform various functions including, but not limited to, analyzing one or more images, determining movement activity associated with a particular joint, an angle of flexion or extension associated with the joint, or other functions as described herein. More particularly, the instructions may configure the control circuit to perform functions such as receiving directly or indirectly signals from one or more sensors indicative of various input conditions and/or various other suitable computer-implemented functions, which enable the processor 142 and/or wireless device 144 to carry out the various functions described herein. An interface can include one or more circuits, terminals, pins, contacts, conductors, or other components for sending and receiving control signals. Moreover, the control circuit may include a sensor interface (e.g., one or more analog-to-digital converters) to permit signals transmitted from any sensors within the system to be converted into signals that can be understood and processed by the processor(s).

In one exemplary embodiment, the controller comprises a processor having a memory device storing computer executable instructions comprising machine learning techniques and the processor is adapted to execute the instructions. The machine learning techniques may include at least one of, e.g., adaptive and non-adaptive noise cancelation of noise in the signals; signal envelope detection; low pass, band-pass, band-stop, and/or high pass digital filters to extract different movement parameters from a data spectrum; or supervised or unsupervised clustering, which may include at least one of k-means, fuzzy c-means artificial neural networks, support vector machine, and/or fuzzy systems to characterize patient movement activity across time (e.g., across a particular rehabilitation or physical therapy plan). Thus, in one embodiment, the processor 142, e.g., through the display 146 of the wireless device 144, could prompt a user to capture images of a particular joint (e.g., knee, hip, shoulder, etc.) overtime and thereby, within a given interval of time, measure changes in movement activity, angles of extension and/or flexion, etc. to determine if a patient is complying with a prescribed at-home rehabilitation program, where additional coaching can then be transmitted to the user to encourage compliance as necessary. Further, to estimate changes in movement activity over time, some statistical and morphological features such as norm, root-mean-square, skewness, kurtosis, entropy, and the like can be used in a machine learning stage to compare present and past images of the patient's joint (e.g., knee, hip, shoulder, etc.) that is being monitored. Also, machine learning based predictive models may be used, e.g., to predict when a patient may need additional coaching based on the level of movement activity over time.

Although FIGS. 4-6, 9-10, and 13-14 show the patient monitoring material 120 in the form of a sleeve and one or more adhesive pads 118, it is also to be understood that the patient monitoring material 120 can be in the form of clothing. For instance, as shown in FIGS. 15A and 15B, the patient monitoring material 120 can be in the form of a shirt 284. Meanwhile, as shown in FIGS. 16A and 16B, the patient monitoring material 120 can also be in the form of pants 286. Further it is to be understood that the patient monitoring material 120 can take the form of any type of clothing or garment so long as the sensors 156 and transmitter 122 can be embedded within or attached to the patient monitoring material 120.

Referring again to FIGS. 17A, 17B, and 18, the functionality of the wireless device 144 with its receiver 150 and processor 142 in conjunction with the patient monitoring material 120, reference indicators 128, sensors 156, and transmitter 122 is discussed in more detail. For instance, FIG. 17A illustrates a front view of the wireless device 144 of FIG. 1 having a display 146 according to one embodiment of the present invention, while FIG. 17B is a front view of the wireless device 144 of FIG. 17A showing an image of reference indicators 128 present on the patient monitoring material 120 in the form of a sleeve 116 around a patient's knee joint 162 aligned with reference guides 148 on the display 146, where the angle α, which measures the amount of flexion in the knee, can be determined via the components in the system 100 of the present invention.

Figure 18:
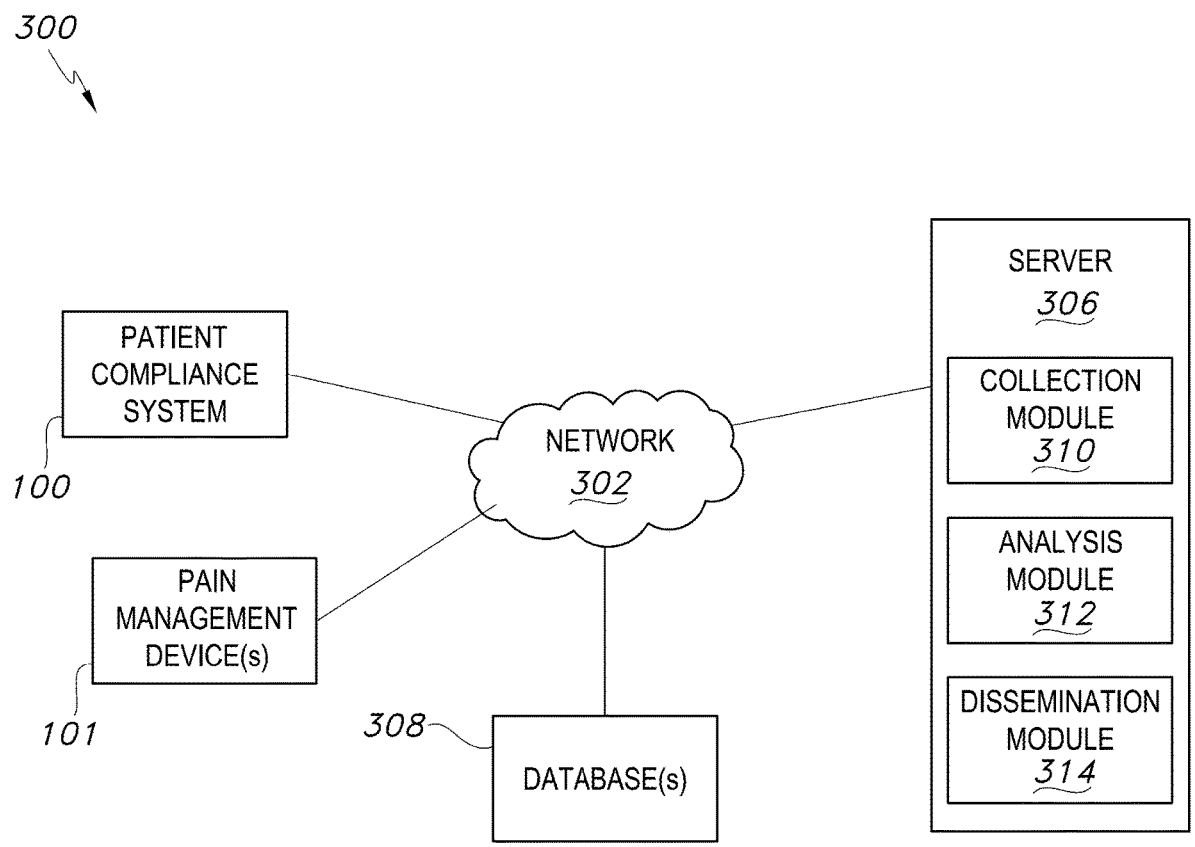
FIG. 18 is a schematic view of a patient management system including the patient monitoring system (e.g., the patient monitoring material and a wireless device) and the optional pain management device of FIG. 1 that may utilize data from one or more devices to monitor a patient's movement activity in order to provide feedback and coaching as well as to develop, augment, and/or adjust a course of physical therapy and/or pain management treatment of the patient in accordance with one embodiment of the present invention.

Referring still to FIG. 18, the schematic diagram view of a representative patient management system 300 that can include the patient monitoring system 100 (e.g., patient monitoring material 120 and a wireless device 144) with a processor 142 and the optional pain management device 101 of FIG. 1 that may utilize data from one or more devices to develop, augment, and/or adjust a course of treatment of the patient is described in more detail. Patient management system 300 includes a network 302 for sending and/or receiving information or data as previously described. A device or system connected through network 302 to a server 306 may provide patient data to server 306 for use in utilizing the patient's health data, such as the patient's movement activity, for developing, augmenting, and/or adjusting the patient's rehabilitation after an orthopedic procedure such as a knee, hip, or shoulder repair or replacement. For example, one or more medical devices or instruments, such as patient monitoring system 100 (including patient monitoring material 120 with sensors 156) and pain management device 101, may be connected to server 306 as depicted in FIG. 18 to provide patient data for use in the patient's treatment. Each system or device may provide medical device-generated patient data to the server 306. Such data may include data from one or more devices used by the patient, such as one or more wearable devices, e.g., for detecting the patient's vital signs, biofeedback, biomarkers, and/or the patient's activity, etc., such as patient monitoring material 120. For example, like the patient monitoring material 120 described above, each medical device may have one or more sensors 156 that output data, which may be provided to server 306 via network 302.

Server 306 is configured to respond to inputs through the systems and devices 100 and 101, etc. to help manage the patient's treatment, e.g., the patient's mobility and range of motion following an orthopedic procedure. The server 306 may be cloud-based, co-located at a hospital site, or located at another appropriate site. The server 306 also may respond to the input of patient data by storing the data in one or more databases 308 communicatively connected to the server 306. As such, the information stored within the database(s) 308 may be information relating, e.g., to the patient's movement activity, level of flexion or extension of a joint, pain level, temperature, other vital signs, or the like.

As shown in FIG. 18, the server 306 can include a number of processing modules. It will be appreciated that the term "module" refers to computer logic utilized to provide specified functionality. Thus, a module can be implemented in hardware, firmware, and/or software controlling a general purpose processor. In one embodiment, the modules are program code files stored on the storage device, loaded into memory, and executed by a processor similar to processor 142 previously described, which may be included within the wireless device 144 or separately located. Alternatively, the modules can be program code files provided from computer program products, e.g., computer executable instructions, which are stored in a tangible computer-readable storage medium such as RAM hard disk or optical or magnetic media. Also, it will be appreciated that embodiments of the server 306 can have different or other modules to the ones described herein, with the described functionalities distributed amongst the modules in a different manner.

Referring to FIG. 18, the server 306 is configured to collect the patient data, e.g., for storage in a database 308, analyze the patient data, and disseminate the patient data. More specifically, the server 306 can include a collection module 310 for collecting patient data from medical devices such as the patience compliance system 100 and the pain management device 101. One or more pieces of patient data may be sent to or received by an analysis module 312 for analysis, which may comprise sorting the data in preparation for analyzing or disseminating the data. For example, the analysis module 312 may use the patient data to develop specific therapies, e.g., the analysis module 312 may use data from the sensors 156 embedded or attached to the patient monitoring material 120 of the patient monitoring system 100 and the pain management device 101 to develop, augment, or adjust the movement activity level and/or type of movement activity, as well as the pain management of the patient. The patient data or the results of the analysis of the patient data may be selectively disseminated or distributed via a dissemination module 314. At least a portion of the patient data may be available to one or more entities, such as the patient, medical professionals, and/or healthcare organization(s).

It should be appreciated that, in some embodiments, the collection module 310, the analysis module 312, and/or the dissemination module 314 may be separate from the server 306. That is, modules 310, 312, 314 may be standalone components of the patient management system 300 in communication with the other components of the system patient management 300, e.g., systems/devices 100 and 101 and databases 308 via network 302. Further, as depicted in FIG. 18, the systems/devices 100 and 101, the server 306, and the database(s) 308 can be connected and/or multiplexed to the network 302, e.g., via direct network or other suitable links. However, the patient management system 300 may have other configurations as well.

A method for monitoring movement activity of a patient is also contemplated by the present invention. The method includes sensing movement activity associated with a joint (e.g., knee joint 162, hip joint 210, shoulder joint 240, etc.)

of the patient via at least one sensor 156 embedded within or attached to a patient monitoring material 120 wherein the patient monitoring material 120 surrounds the joint; transmitting the movement activity associated with the joint of the patient to a device (e.g., a wireless device 144 such as a smartphone, tablet, PC, etc.); and determining parameters associated with compliance with a rehabilitation or physical therapy program based on the movement activity associated with the joint of the patient via a processor 142. Further, the parameters associated with compliance with the rehabilitation or physical therapy program can include an angle of extension of the joint, an angle of flexion of the joint, a total number of minutes during which the patient is active over a predetermined time period, or a combination thereof.

In addition, the method can include capturing an image of the joint via an image capture mechanism 140 included in the device 144; processing the image via the processor 142; and displaying information to a user regarding the movement activity associated with the joint of the patient on a display 146 on the wireless device 144. Further, at least one reference guide 148 can be displayed on the display 146 to assist a user in capturing the image and at least one reference indicator 128 on the patient monitoring material 120 can be aligned within the at least one reference guide 148 when capturing the image. Additionally, the processor 142 can be configured to process the image to determine an angle of extension of the joint or an angle of flexion of the joint, and processing the image can include comparing the image to one or more stored images to determine, for instance, the angle of extension or the angle of flexion of the joint. Moreover, the method can include providing coaching or instructions (e.g., in the form of verbal instructions delivered from the device 144 via the processor 142, pictorial or graphic instructions displayed on the device 144 via the process 142, etc.) to the patient based on the movement activity associated with the joint of the patient.

Further, it is to be understood that the patient monitoring system 100 described in the present application can be utilized in conjunction with the system and method described in U.S. Patent Application Provisional Application No. 62/710,464, filed on Feb. 16, 2018 and entitled "Post-Operative Monitoring via Patient Reported Outcomes," which is incorporated herein by reference in its entirety.

The present invention has been described both in general and in detail by way of examples. These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A system for monitoring movement activity of a patient, the system comprising:
   a patient monitoring material for determining movement activity associated with a joint of the patient, wherein the patient monitoring material includes a plurality of sensors for sensing the movement activity associated with the joint of the patient, a transmitter, and at least one reference indicator located on a portion of the patient monitoring material, wherein the patient monitoring material comprises a sleeve extending above and/or below the joint of the patient, one or more adhesive pads, a shirt, pants, or a combination thereof;
   a mobile device comprising a receiver and a processor, wherein the transmitter transmits the movement activity associated with the joint of the patient to the receiver, wherein the processor is configured to:
      prompt the patient to capture a plurality of images of the joint via a camera of the mobile device during a plurality of corresponding time intervals,
      determine an angle of extension or an angle of flexion of the joint in each of the plurality of images,
      determine, using a clustering machine learning model, parameters associated with compliance with a rehabilitation or physical therapy program by correlating the movement activity with the respective angles of extension or angles of flexion in each of the plurality of images, stored movement activity associated with the patient, and biometric data for the patient, wherein the determined parameters include a target angle of extension of the joint, a target angle of flexion of the joint, a total number of minutes during which the patient is active over a predetermined time period, and an estimated pain level, and
      determine whether the patient is in compliance with the rehabilitation or physical therapy program based, at least in part on, a change in at least one of the determined parameters.

2. The system of claim 1, wherein the sleeve includes a stretchable material for conforming around the joint.

3. The system of claim 1, wherein the joint is a knee joint, a hip joint, or a shoulder joint.

4. The system of claim 1, wherein the at least one sensor includes a dielectric elastomer accelerometer, a laser accelerometer, a low frequency accelerometer, an optical accelerometer, a piezoelectric accelerometer, a resonance accelerometer, a surface acoustic wave accelerometer, a surface micromachined capacitive accelerometer, a thermal accelerometer, a triaxial accelerometer, a potentiometric type accelerometer, a strain gauge sensor, or a combination thereof.

5. The system of claim 1, wherein the at least one reference indicator is a symbol.

6. The system of claim 1, wherein the mobile device includes a camera configured to capture an image of the joint.

7. The system of claim 6, wherein the mobile device further includes a display to provide information about the image.

8. The system of claim 7, further wherein the processor displays at least one reference guide on the display to assist a user in utilizing the camera to capture the image.

9. The system of claim 8, wherein the at least one reference indicator is capable of alignment within the at least one reference guide on the display when capturing the image.

10. The system of claim 6, wherein the processor is configured to process the image to determine the angle of extension of the joint or the angle of flexion of the joint.

11. The system of claim 10, wherein the image is compared to one or more stored images.

12. The system of claim 1, wherein the mobile device is wireless.

13. The system of claim 1, wherein the processor provides coaching or instructions to the patient based on the movement activity associated with the joint of the patient.

14. A method for monitoring movement activity of a patient, the method comprising:
   sensing movement activity associated with a joint of the patient via at least one sensor embedded within or attached to a patient monitoring material, wherein the patient monitoring material surrounds the joint, wherein at least one reference indicator is located on a portion of the patient monitoring material, wherein the patient monitoring material comprises a sleeve extending above and/or below the joint of the patient, one or more adhesive pads, a shirt, pants, or a combination thereof;

transmitting the movement activity associated with the joint of the patient to a mobile device;

prompting the patient to capture a plurality of images of the joint via a camera of the mobile device during a plurality of corresponding time intervals;

determining an angle of extension of an angle of flexion of the joint in each of the plurality of images;

determining, using a machine learning model, parameters associated with compliance with a rehabilitation or physical therapy program by correlating the movement activity with the respective angles of extension or angles of flexion in each of the plurality of images, stored movement activity associated with the patient, and biometric data for the patient, wherein the determined parameters, wherein the determined parameters include a target angle of extension of the joint, an angle of flexion of the joint, a total number of minutes during which the patient is active over a predetermined time period, and an estimated pain level; and determining whether the patient is in compliance with the rehabilitation or physical therapy program based, at least in part on, a change in at least one of the determined parameters.

15. The method of claim 14, the method further comprising:

capturing an image of the joint via a camera included in the device;

processing the image via a processor of the mobile device; and displaying information to a user regarding the movement activity associated with the joint of the patient on a display of the mobile device.

16. The method of claim 15, further wherein at least one reference guide is displayed on the display to assist a user in capturing the image.

17. The method of claim 16, wherein at least one reference indicator on the patient monitoring material is aligned within the at least one reference guide when capturing the image.

18. The method of claim 15, wherein the processor is configured to process the image to determine the angle of extension of the joint or the angle of flexion of the joint.

19. The method of claim 15, wherein processing the image comprises comparing the image to one or more stored images.

20. The method of claim 14, the method further comprising:

providing coaching or instructions to the patient via the device based on the movement activity associated with the joint of the patient.

* * * * *